United States Patent
Okamoto

(10) Patent No.: US 8,086,418 B2
(45) Date of Patent: Dec. 27, 2011

(54) IMPERFECT COMBUSTION DETECTING DEVICE

(75) Inventor: Hideo Okamoto, Nagoya (JP)

(73) Assignee: Rinnai Corporation, Nagoya-shi (JP)

( * ) Notice: Subject to any disclaimer, the term of this patent is extended or adjusted under 35 U.S.C. 154(b) by 541 days.

(21) Appl. No.: 12/391,736

(22) Filed: Feb. 24, 2009

(65) Prior Publication Data

US 2009/0211334 A1  Aug. 27, 2009

(30) Foreign Application Priority Data

Feb. 25, 2008  (JP) .................... 2008-043458

(51) Int. Cl.
*G01C 25/00* (2006.01)
*G01N 27/00* (2006.01)

(52) U.S. Cl. .................. 702/116; 73/1.06; 204/401

(58) Field of Classification Search ............... 73/1.06, 73/23.31; 702/116; 340/632; 204/401
See application file for complete search history.

(56) References Cited

U.S. PATENT DOCUMENTS

| | | | | |
|---|---|---|---|---|
| 6,076,389 A | * | 6/2000 | Kaneko | 73/1.06 |
| 6,200,443 B1 | * | 3/2001 | Shen et al. | 204/401 |
| 6,948,352 B2 | * | 9/2005 | Rabbett et al. | 73/1.06 |
| 7,090,755 B2 | * | 8/2006 | Inoue et al. | 204/401 |
| 7,499,821 B2 | * | 3/2009 | Kleefstra | 702/116 |
| 7,581,946 B2 | * | 9/2009 | Donnelly et al. | 73/1.06 |
| 7,817,499 B2 | * | 10/2010 | Solhjoo et al. | 368/10 |
| 2005/0016253 A1 | * | 1/2005 | Anilovich et al. | 702/116 |
| 2007/0109143 A1 | * | 5/2007 | Klofer et al. | 340/665 |
| 2011/0005929 A1 | * | 1/2011 | Tice | 73/1.06 |

FOREIGN PATENT DOCUMENTS

JP  08-014556  1/1996

* cited by examiner

*Primary Examiner* — Lisa Caputo
*Assistant Examiner* — Punam Roy
(74) *Attorney, Agent, or Firm* — Rankin, Hill & Clark LLP

(57) ABSTRACT

An imperfect combustion detecting device includes a destructive current supplying means which supplies, under a condition that it is determined by a useful life determining means that a deterioration status corresponding value matches a use limit value, destructive current to a sensor in order to melt down a part of a circuit that configures the sensor. When it is determined that the sensor is no longer capable of performing a normal CO level detecting function, the sensor is destroyed to the extent rendering the CO level detecting function of the sensor lost to an unrecoverable level.

12 Claims, 2 Drawing Sheets

IMPERFECT COMBUSTION DETECTING DEVICE

BACKGROUND OF THE INVENTION

1. Field of the Invention

The present invention relates to an imperfect combustion detecting device.

2. Description of the Related Art

As a conventional imperfect combustion detecting device, a kind that uses a CO sensor to detect a CO level in combustion gas, having been generated by a burner in a combustion apparatus, is known. With such imperfect combustion detecting device, a deterioration status of the CO sensor is detected. When it is determined that deterioration of the CO sensor has progressed to the extent that the normal detecting function cannot be expected in the near future, the imperfect combustion detecting device lets out a maintenance request to notify a user that the CO sensor needs to be changed (e.g. Japanese Patent Laid-Open No. H08-14556).

However, such maintenance request is not let out after the CO sensor has reached the end of its useful life at which point the normal detecting function is practically no longer available, but is let out in advance when it is determined that the CO sensor has reached the end of its predetermined "probable useful life", while the CO sensor is still capable of performing the normal detecting operation.

Therefore, even after the maintenance request has been let out, as long as functions of the combustion apparatus other than the CO sensor is normally operating, there is a possibility that the user or service provider keeps using the combustion apparatus without changing the CO sensor.

SUMMARY OF THE INVENTION

It is therefore an object of the present invention to provide an imperfect combustion detecting device which is capable of causing a CO level detecting function of a sensor to be lost to an unrecoverable level when the sensor has reached the end of its probable useful life.

According to an aspect of the present invention, an imperfect combustion detecting device comprises: a sensor which detects, when being energized, a CO level in combustion gas as generated at a burner in a combustion apparatus; a useful life determining means which compares a use limit value, which is a value corresponding to a predetermined probable useful life of the sensor and being stored in a memory section, with a deterioration status corresponding value, which is a value inputted depending on changes in deterioration status of the sensor, in order to determine as to whether the deterioration status corresponding value matches the use limit value; and a destructive current supplying means which supplies, under a condition in which it is determined by the useful life determining means that the deterioration status corresponding value matches the use limit value, destructive current to the sensor in order to destroy a circuit that configures the sensor.

With this imperfect combustion detecting device, the destructive current is supplied to the sensor by the destructive current supplying means when the useful life determining means determines that the deterioration status corresponding value and the use limit value match. Since the circuit that configures the sensor is destroyed by this destructive current, the sensor is destroyed to the extent that its CO level detecting function is rendered unrecoverable.

According to another aspect of the present invention, it is possible that the imperfect combustion detecting device further comprises a detecting circuit which detects as to whether the circuit configuring the sensor is broken and outputs the detected result. With such arrangement, the detecting circuit detects as to whether the circuit that configures the sensor has been destroyed due to the destructive current, and output the detected result. By this output, the combustion apparatus is able to recognize that the sensor has been destroyed, and thus is able to perform processes, such as a process to stop the power supply to the burner, etc., which are necessary in letting the combustion apparatus operate safely.

According to another aspect of the present invention, it is possible that the imperfect combustion detecting device further comprises an announcing means which warns a user that the sensor will be destroyed in the near future. In such case, a use limit warning value as being a value to be used in warning the coming of the end of the probable useful life of the sensor is stored in the memory section. When it is determined by the useful life determining means that the deterioration status corresponding value matches the use limit warning value, the warning indicating that the sensor has come close to the end of its probable useful life can be let out by the announcing means.

With such arrangement, when it comes close to the end of the probable useful life of the sensor, the useful life determining means determines that the deterioration status corresponding value matches the use limit warning value, and the announcing means announces that the sensor has come close to the end of its probable useful life based on the determination result. Therefore, since the user can be warned that the sensor will be destroyed in the near future, the user has the chance to take a measure and change the sensor in advance.

According to another aspect of the present invention, it is possible that the destructive current supplying means in the imperfect combustion detecting device is arranged in a way including a power source circuit which supplies the sensor with power for enabling the sensor to perform a CO level detecting function, and a voltage amplifying circuit which amplifies a voltage applied to the sensor by the power source circuit based on the determination made by the useful life determining means, and in such a way that destructive current is supplied to the sensor from the power source circuit due to amplification operation performed by the voltage amplifying circuit.

With such structure, since the existing power source circuit that is necessary for the usual detecting operation by the sensor is used, it is not necessary to have an exclusive power source circuit for the purpose of supplying the destructive current.

According to another aspect of the present invention, it is possible to arrange such that the circuit that configures the sensor melts down and becomes disconnected due to being supplied with the destructive current, and that the detecting circuit detects that a part of the circuit that configures the sensor is being disconnected.

With such arrangement, it is possible to detect the disconnection of the circuit that configures the sensor, whereby it is possible to confirm that the sensor is being destroyed.

DETAILED DESCRIPTION OF THE PREFERRED EMBODIMENTS

First Embodiment

Figure 1:
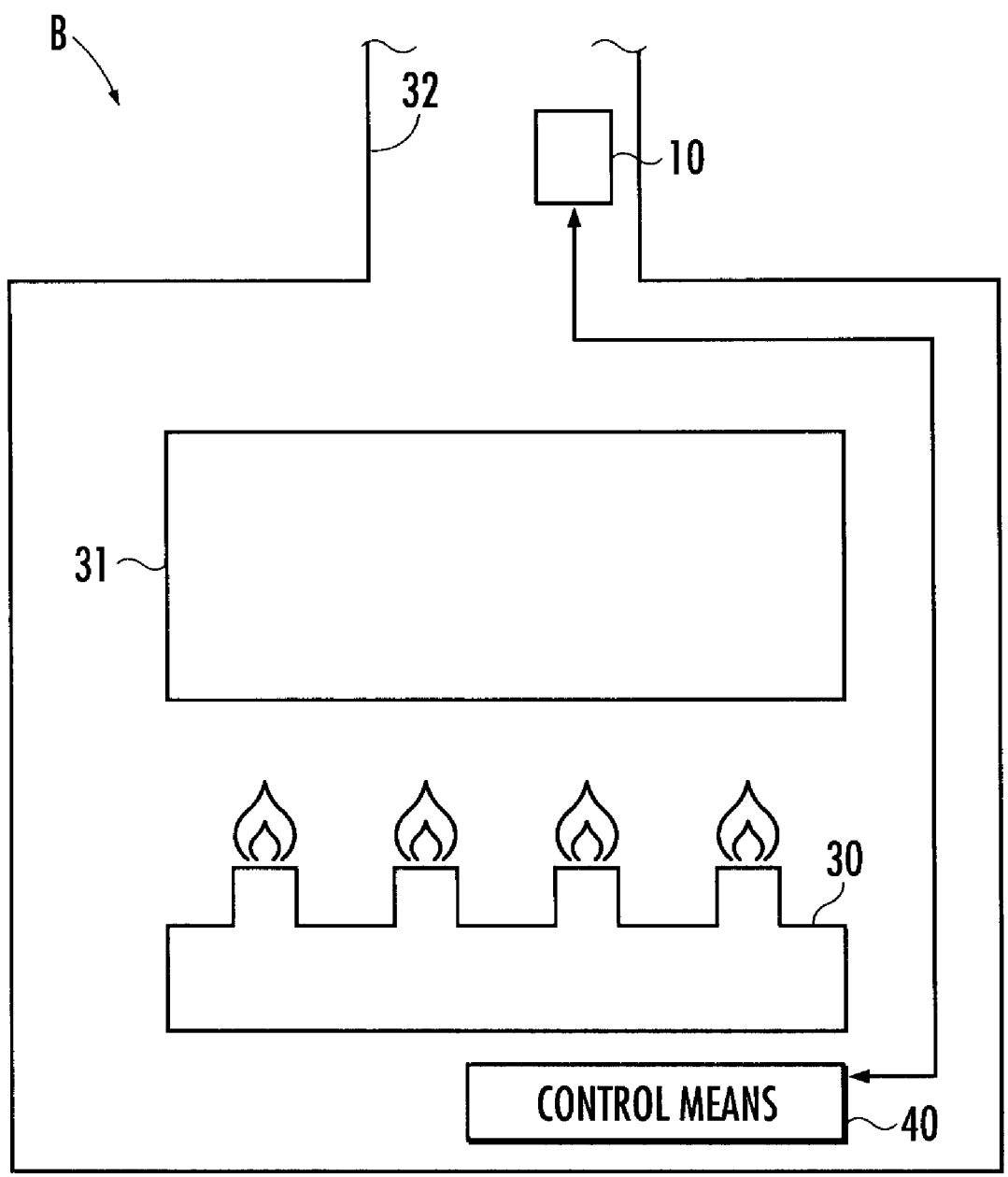
FIG. 1 is a schematic view of a water heater.
Figure 2:
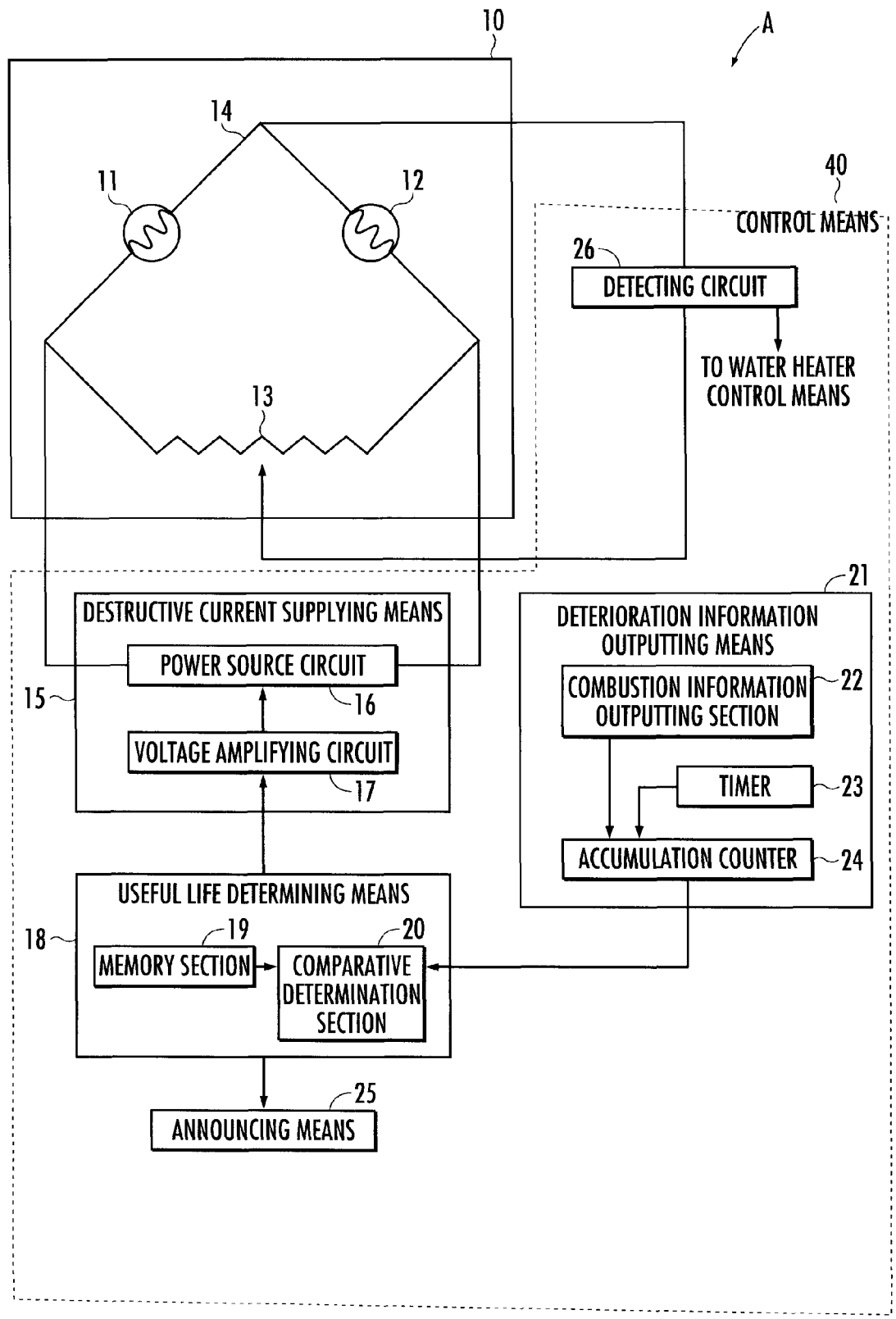
FIG. 2 is a block diagram illustrating a structure of an imperfect combustion detecting device according to a first embodiment.

FIG. 1 and FIG. 2 are diagrams for describing a first embodiment of the present invention. As shown in FIG. 1, a water heater B, as being one example of a combustion apparatus that has an imperfect combustion detecting device A according to the first embodiment, includes a burner 30, a heat exchanger 31 arranged above the burner 30, an exhaust path 32 for discharging combustion gas generated at the burner 30, and a control means 40 that controls the operation of the water heater B. A sensor 10, which is a part of the imperfect combustion detecting device A, is arranged in the exhaust path 32. This sensor 10 is arranged in order to detect a CO (carbon monoxide) level in combustion gas. Based on a detection signal from the sensor 10, the imperfect combustion detecting device A detects as to whether or not the water heater B is causing any imperfect combustion.

The control means 40 not only enables respective functions of the imperfect combustion detecting device A, which will be described later on, but also implements operation controls on the water heater B including ignition control, temperature control, and so forth. Therefore, while the control means 40 is used as a means to enable respective functions of the imperfect combustion detecting device A, it also functions as a means to control the water heater B as it controls fuel supply to the burner 30, ignition timing of the burner 30, and so forth. In the following, a part of the control means 40 that functions as a means to control the water heater B is referred to as a water heater control means.

In a case when a user starts using the water heater B, the water heater control means, prior to supplying fuel to the burner 30 and igniting the burner 30, performs an initial check on the water heater B in order to determine as to whether the water heater B is capable of operating safely. Checking items include a sensor operability confirmation for confirming as to whether the sensor 10 is capable of operating normally, i.e. whether the sensor 10 has no problem such as disconnection, or the like. Moreover, in a case when the imperfect combustion detecting device A detects imperfect combustion, the water heater control means performs predetermined processes such as a process to stop supplying fuel to the burner 30 in order to stop the combustion.

The imperfect combustion detecting device A according to the present embodiment includes the sensor 10 and the control means 40. In addition to the primary Co level detecting function for detecting the CO level in the combustion gas for the purpose of detecting imperfect combustion at the water heater B, the control means 40 has a sensor destroying function. With this sensor destroying function, it is determined as to whether the sensor 10 has reached the end of its predetermined probable useful life, and in a case when it is determined that the sensor 10 has reached the end of its probable useful life, the sensor 10 is destroyed whereby the CO level detecting function of the sensor 10 is rendered unrecoverable. The sensor 10 having reached the end of its probable useful life does not mean that the sensor 10 is no longer capable of actually exercising the normal CO level detecting function, but it means that the sensor 10 is expected to become unable to exercise the normal CO level detecting function in the near future, although the sensor is capable of exercising the normal CO level detecting function for the moment. In the following, a structure enabling the CO level detecting function and the sensor destroying function will be described.

In FIG. 2, the imperfect combustion detecting device A has a detecting circuit 26, a destructive current supplying means 15, a useful life determining means 18, a deterioration information outputting means 21, the control means 40 having an announcing means 25, and the sensor 10. It is to be noted that in FIG. 2, only the structure of the control means 40 for enabling the functions of the imperfect combustion detecting device A is being focused.

The sensor 10 is a so-called catalytic combustion type sensor with a known structure. The sensor 10 is configured with a bridge circuit where a gas detector element 11 and a temperature compensation element 12, each of which having a known form where a platinum coil (not shown) is embedded in a catalyst, are series-connected, while a variable resistor 13 and both the elements 11 and 12 are parallel-connected. A power source circuit 16 and the detecting circuit 26 are connected to the bridge circuit of the sensor 10. In order to supply the bridge circuit with power that is necessary for the sensor 10 to perform ordinary CO level detection, the power source circuit 16 applies a predetermined voltage (e.g. 2 V) to the series circuit, where the elements 11 and 12 are connected, and to the variable resistor 13. The detecting circuit 26 is connected to an output terminal 14 as connected in between the elements 11 and 12, and with the variable resistor 13. When current starts flowing as an electric potential difference is generated between the output terminal 14 and the variable resistor 13, the corresponding current value is outputted to the detecting circuit 26 as a CO level detection signal. The detecting circuit 26 detects the CO gas concentration (CO level) based on the inputted CO level detection signal. When the value of the detected CO level exceeds a specified value, the detecting circuit 26 outputs a stop signal for stopping fuel supply to the burner 30. When this stop signal is received, the water heater control means stops the fuel supply to the burner 30 and let the combustion be stopped.

In using the sensor 10, the variable resistor 13 is adjusted in advance. By such adjustment, even when the power source circuit 16 supplies the bridge circuit with power with a voltage that is necessary for the CO level detection, it is arranged such that the CO level detection signal is not outputted from the bridge circuit when the burner 30 is not under combustion. When the CO gas is generated, the CO gas touches the catalyst of the gas detector element 11 whereby the catalyst starts generating heat and a resistance value of the platinum coil starts rising. This resistance value becomes higher as the amount of CO gas touching the catalyst becomes larger. That is, the resistance value becomes higher as the CO gas concentration in the combustion gas that passes through the exhaust path 32 becomes higher. When the resistance value of the platinum coil rises, an electric potential difference is generated between the output terminal 14 and the variable resistor 13, whereby current starts flowing, and a CO level detection signal with a value corresponding to the CO gas concentration is inputted to the detecting circuit 26.

The detecting circuit 26 also functions as a disconnection detecting means for detecting possible disconnection in the bridge circuit that configures the sensor 10. When the platinum coil of the gas detector element 11 or the temperature compensation element 12 in the bridge circuit is disconnected, even when the burner 30 is not under combustion, an electric potential difference is generated between the output terminal 14 and the variable resistor 13, whereby current starts flowing, and the corresponding current value is outputted to the detecting circuit 26 as a disconnection detection signal.

When the disconnection detection signal is received, the detecting circuit 26 notifies the water heater control means about the reception of the disconnection detection signal. When this notification is received, the water heater control means recognizes that the sensor 10 has been disconnected and thus let the water heater B become unusable. Specifically, in a case when the water heater B is being used, for example, the water heater control means determines, after a predetermined period of time has passed since the reception of the notification, as to whether the water heater B is being used. When it is determined that the water heater B is being used, the water heater control means stops the fuel supply to the burner 30 and let the combustion be stopped. In a case when the water heater B is not being used (being unused), at the time the user next attempts to use the water heater B, the water heater control means performs the above-described initial check prior to supplying fuel to the burner 30 and igniting the burner 30. The initial check includes a determination on as to whether or not the sensor 10 is disconnected. If it is determined through the initial check that the sensor 10 is being disconnected, the water heater control means does not supply fuel to the burner 30 or ignite the burner 30, for it is dangerous to operate the water heater B while possible imperfect combustion is not able to be detected. Through the initial check, if it is determined that the sensor 10 is not being disconnected and safety of the other functions is confirmed, the water heater control means controls fuel supply to the burner 30 and ignition of the burner 30 to let the water heater B start operating.

Meanwhile, in the case when disconnection of the sensor 10 is detected by the detecting circuit 26, it is possible to let the user know that the sensor 10 has been disabled. Specifically, as the water heater control means is notified by the detecting circuit 26 that disconnection of the sensor 10 has been detected, the water heater control means notifies the user that the sensor 10 has been disabled, by using a remote control section (not shown) as being arranged at the water heater B. The notification can be let out by means of displaying a text message, etc. on a liquid crystal display section of the remote control section; outputting sounds from a speaker arranged at the remote control section; letting a lamp arranged at the remote control section flicker or light up; or sounding a buzzer arranged at the remote control section. Furthermore, it is also possible to direct the notification to a maintenance engineer instead of the user. That is, the water heater control means can let a kind of signal that can indicate the destruction of the sensor 10 on a special device the maintenance engineer uses to check the water heater B for any abnormality outputted.

The destructive current supplying means 15 includes the above-mentioned power source circuit 16 and a voltage amplifying circuit 17. The voltage amplifying circuit 17 is a circuit for amplifying voltage of the power supplied to the bridge circuit from the power source circuit 16. In performing the usual CO gas concentration detection, a signal for enabling voltage amplification is not outputted to the power source circuit 16 from the voltage amplifying circuit 17, and thus the power source circuit 16 supplies the bridge circuit with power with a comparatively low voltage (2 V) that is necessary for the gas detection. The platinum coil of the gas detector element 11 or the temperature compensation element 12 does not melt down by this low voltage current.

On the contrary, in a case when the destructive current supplying means 15 receives from the useful life determining means 18, which will be described later on, a signal indicating that the sensor 10 has reached the end of its "probable useful life", a signal requesting amplification of voltage directed to the power source circuit 16 is outputted from the voltage amplifying circuit 17. In response to this signal, the power source circuit 16 supplies the bridge circuit of the sensor 10 with power (destructive current) with a voltage (e.g. 20 V) that is considerably higher than the voltage necessary for the usual gas detection. The voltage at this time is high enough to melt down the platinum coil of the gas detector element 11 or the temperature compensation element 12.

In the present embodiment, the destructive current supplying means 15 has the power source circuit 16 for supplying the sensor 10 with power for exercising the CO level detecting function, and the voltage amplifying circuit 17 for amplifying, based on the determination made by the useful life determining means 18, the voltage applied to the sensor 10 by the power source circuit 16, and due to the amplification operation by the voltage amplifying circuit 17, a high voltage destructive current can be supplied to the sensor 10 from the power source circuit 16. With this structure, therefore, it is not necessary to have a different power source circuit exclusively for supplying the destructive current in addition to the power source circuit 16.

The useful life determining means 18 has a memory section 19 and a comparative determination section 20. In the memory section 19, three use limit values (i.e. use limit values corresponding to the "probable useful life" of the sensor 10), which are used as indexes in determining as to whether the sensor 10 has reached the end of its predetermined probable useful life, are being stored in advance. The three use limit values can be obtained from a usual usage pattern of the water heater B, and these values are being set based on information with which the correspondence relation with the deterioration status of the sensor 10 can be estimated. Specifically, the three values are the cumulated number of ignitions of the burner 30 in the water heater B, cumulated combustion time of the burner 30, and elapsed time (elapsed years) from the time of installation or starting of use of the water heater B. These values can be set based on results of various tests.

The comparative determination section 20 compares the above-mentioned three use limit values with three deterioration status corresponding values as inputted from the deterioration information outputting means 21, which will be described later on, depending on changes in the deterioration status of the sensor 10. Then the comparative determination section 20 determines as to whether each of the deterioration status corresponding values matches the corresponding use limit value. Based on this determination result, the useful life determining means 18 determines as to whether the sensor 10 has reached the end of its "probable useful life".

As one example of a way to determine that the sensor 10 has reached the end of its "probable useful life", it is possible to make the determination when one of the following three conditions is met. A first condition is that one of the three deterioration status corresponding values matches the use limit value; a second condition is that two of the three deterioration status corresponding values match the use limit values; and a third condition is that all of the three deterioration status corresponding values match the use limit values.

The deterioration information outputting means 21 has a combustion information outputting section 22, a timer 23, and an accumulation counter 24. The combustion information outputting section 22 outputs to the accumulation counter 24 information (data) that is necessary for deriving the cumulated number of ignitions and the cumulated combustion time among the above-mentioned three use limit values. That is, the combustion information outputting section 22 outputs an ignition information signal to the accumulation counter 24 each time the burner 30 is ignited. The accumulation counter 24, where the ignition information signal is received, cumulates the number of times it has received the ignition information signal, and outputs to the comparative determination section 20 the cumulated number of ignitions as a deterioration status corresponding value.

Furthermore, at each ignition of the burner 30, the combustion information outputting section 22 outputs to the accumulation counter 24 combustion time information including the time that has taken from ignition to extinction (i.e. combustion time) as a combustion time information signal. When the combustion time information signal is received, the accumulation counter 24 cumulates the combustion time as included in the combustion time information signal, and outputs to the comparative determination section 20 the cumulated combustion time as a deterioration status corresponding value which is different from that of the cumulated number of ignitions.

At each elapse of a predetermined period of time, the timer 23 outputs to the accumulation counter 24 an elapsed time information signal that indicates the elapse of the predetermined period of time. That is, the timer 23 outputs the elapsed time information signal to the accumulation counter 24 at each predetermined time interval (elapsed time interval). When the elapsed time information signal is received, the accumulation counter 24 cumulates the time that corresponds to the elapsed time interval at which point the elapsed time information signal is received, and outputs to the comparative determination section 20 the cumulated elapsed time as a deterioration status corresponding value which is different from that of either the cumulated number of ignitions or the cumulated combustion time.

The imperfect combustion detecting device A has an announcing means 25 for giving the user a warning that the sensor 10 will be destroyed in the near future. In order to let this announcing means 25 function, the memory section 19 that configures the above-mentioned useful life determining means 18 stores therein three use limit warning values. As with the case of the above-described use limit values, these three use limit warning values are the cumulated number of ignitions of the burner 30 in the water heater B, cumulated combustion time of the burner 30, and elapsed time (elapsed years) from the time of installation or starting of use of the water heater B. Each of the three use limit warning values is being set to a smaller value than the corresponding use limit value.

The comparative determination section 20 compares these three use limit warning values with the above-mentioned three deterioration status corresponding values, and determines as to whether each of the deterioration status corresponding values matches the corresponding use limit warning value. Based on this determination result, the useful life determining means 18 determines as to whether it has come to a situation where the user should be given a warning that the sensor 10 will be destroyed in the near future. Thus, in addition to the function of determining as to whether the sensor 10 has reached the end of its probable useful life, the useful life determining means 18 has the function of determining as to whether it has come to a situation where a warning that the sensor 10 will be destroyed in the near future should be let out.

The way of determining in this case is similar to that in the above-described case of determining as to whether the sensor 10 has reached the end of its probable useful life. The only difference between the two cases is that in this case, the use limit warning values are used instead of the use limit values. Accordingly, a description for the way of determining in this case will be omitted.

When it is determined that it has come to a situation where a warning that the sensor 10 will be destroyed in the near future should be let out, the useful life determining means 18 outputs an announcing request signal directed to the announcing means 25 for requesting announcing operation. Specific examples of the announcing means 25 are similar to the above-described means for notifying that disconnection (destruction) of the sensor 10 has been detected. In this case therefore, the warning can be let out, when the announcing request signal is received by a remote control section (not shown), by means of displaying a text message, etc. on a liquid crystal display section of the remote control section; outputting sounds from a speaker arranged at the remote control section; letting a lamp arranged at the remote control section flicker or light up; or sounding a buzzer arranged at the remote control section, whereby the user can be warned that the sensor 10 will be destroyed in the near future.

When it is determined at the useful life determining means 18 that the deterioration status corresponding values as inputted from the deterioration information outputting means 21 match the use limit warning values as stored in the memory section 19, the announcing means 25 starts operating, whereby the user is given a warning that the sensor 10 will be destroyed in the near future. Thereby, the user is able to change the sensor 10 in advance before the water heater B becomes unusable due to the destruction of the sensor 10, and while the sensor 10 is still operating normally.

As described above, the use limit warning values which are used as references in determining as to whether a warning about future destruction of the sensor 10 should be let out are being set to smaller values than the use limit values which are used as references in determining as to whether the sensor 10 should be destroyed. Therefore, there is some leeway in terms of the number of ignitions and combustion or usable time from the point the warning of the future destruction of the sensor 10 has been let out to the point the sensor 10 is actually destroyed. Accordingly, the water heater B can be used normally within the leeway number of times or within a leeway time period. While waiting for the time that the sensor 10 is destroyed, it is possible to let the user know the leeway number of ignitions that are available with the burner 30, a leeway time period (combustion leeway time period) allowed for combustion of the burner 30, and change in a leeway time period (usable leeway time period) that indicates a remaining usable time period of the water heater B which becomes shorter regardless of whether the water heater B is used or not.

More specifically, in a case of notifying the user of the leeway number of ignitions, the comparative determination section 20 calculates a difference between the cumulated number of ignitions and the use limit value corresponding to the cumulated number of ignitions, on the basis of which the useful life determining means 18 reports to the announcing means 25 the difference calculated by the comparative determination section 20 as the leeway number of ignitions. In a case of notifying the user of the combustion leeway time period, the comparative determination section 20 calculates a difference between the cumulated combustion time and the corresponding use limit value, on the basis of which the useful life determining means 18 reports to the announcing means 25 the difference calculated by the comparative determination section 20 as the combustion leeway time period. In a case of notifying the user of the usable leeway time period, the comparative determination section 20 calculates a difference between the elapsed time and the use limit value corresponding to the elapsed time, on the basis of which the useful life determining means 18 reports to the announcing means 25 the difference calculated by the comparative determination section 20 as the usable leeway time period.

When the leeway number of ignitions, the combustion leeway time period or the usable leeway time period is reported, the announcing means 25 notifies the user of the leeway number of ignitions, the combustion leeway time period or the usable leeway time period by means of displaying the leeway number of ignitions, the combustion leeway time period or the usable leeway time period through a text message, etc. on a liquid crystal display section of a remote control section (not shown); indicating the leeway number of ignitions, the combustion leeway time period or the usable leeway time period by sounds outputted from a speaker arranged at the remote control section; or the like.

In a case when the user keeps using the water heater B without changing the sensor 10 regardless of the warning about the future destruction of the sensor 10, and when it comes to the point that the deterioration status corresponding value as inputted to the useful life determining means 18 from the deterioration information outputting means 21 matches the use limit value as stored in the memory section 19, the useful life determining means 18 determines that the sensor 10 has come to the end of its probable useful life. At this time, the destructive current supplying means 15 lets the voltage amplifying circuit 17 output a signal for requesting the power source circuit 16 to perform voltage amplification. In response to this signal, the power source circuit 16 supplies the bridge circuit of the sensor 10 with a high voltage destructive current. Thereby, the gas detector element 11 or the temperature compensation element 12 is disconnected, resulting in destroying the sensor 10 to the extent rendering the CO level detecting function of the sensor 10 unrecoverable. As the sensor 10 becomes disconnected, the detecting circuit 26 functions as the disconnection detecting means and detect that the sensor 10 has become disconnected.

When the disconnection of the sensor 10 is detected, the detecting circuit 26 notifies the water heater control means about the reception of the disconnection detection signal. Thereby, as mentioned earlier, in a case when the water heater B is being used, the water heater control means determines, after a predetermined period of time has passed since the reception of the notification, as to whether the water heater B is being used. When it is determined that the water heater B is being used, the water heater control means stops the fuel supply to the burner 30 and let the combustion be stopped. When it is determined that the water heater B is unused, at the time the user next attempts to use the water heater B, the water heater control means performs the above-described initial check prior to supplying fuel to the burner 30 and igniting the burner 30. In this case, however, the water heater control means recognizes that the sensor 10 has been destroyed, and thus the water heater control means does not supply fuel to the burner 30 or ignite the burner 30. Thereby, when the sensor 10 has been destroyed by having the bridge circuit thereof being supplied with the destructive current from the destructive current supplying means 15, fuel supply to the burner 30 or ignition of the burner 30 is stopped, and thus the safety of the water heater B is maintained.

Other Embodiments

The present invention is not to be considered limited to the above-described first embodiment. For example, the following embodiments can be considered as within the technical scope of the present invention. In addition to the following examples, the present invention can also be practiced in other various forms without departing from the scope of the invention.

It is not necessary that the combustion apparatus should be a water heater, while it could be a heating apparatus (e.g. gas stove, fan heater, etc.), a bath heater, or the like.

It is not necessary that the sensor should be a catalytic combustion type, while it could also be a hot wire semiconductor type (fixed heat conduction type).

When there is a possibility that the combustion apparatus will be used in an environment where substances that can greatly deteriorate the sensitivity of the sensor by being attached to the sensor, such as microparticles of a silicon compound, are found floating in relatively large amounts, it is possible to arrange a microparticle sensor in the vicinity of the sensor in order to detect the floating amount of microparticles which could cause the sensitivity deterioration, and obtain the use limit values and the deterioration status corresponding values based on the values detected by such microparticle sensor.

According to the first embodiment, in determining as to whether the sensor has reached the end of its probable useful life, it is determined that the sensor has reached the end of its probable useful life in an indirect way, based on the information (e.g. cumulated number of combustions at the combustion apparatus, cumulated combustion time at the combustion apparatus, elapsed years from the time of installation of the combustion apparatus, etc.) with which the correspondence relation with the deterioration status of the sensor can be estimated. However, the present invention is not limited to such condition, while the end of the probable useful life of the sensor can also be determined based on the actual deterioration status of the sensor. Specifically, by monitoring a relation between a voltage value outputted from the sensor as a detection signal and an element (e.g. a flow rate of fuel supplied to the burner, a flow rate of air flowing into the burner, or the like) that can influence the combustion status of the burner, it is possible to keep track of change in the correlation between the two, and thus it is possible to directly detect the actual deterioration status of the sensor based on the change in the correlation between the two. More specifically, if the fuel is supplied to the burner by a constant amount, the voltage value outputted from the sensor as the detection signal decreases as the sensor deteriorates. Therefore, the use limit value is set according to the correlation between the sensor deterioration-induced decrease in the voltage value outputted as the detection signal and the flow rate of fuel supplied to the burner, the flow rate of air flowing into the burner, or the like, whereby it is possible to determine that the sensor has reached to the end of its probable useful life when the set use limit value and the voltage value outputted from the sensor as the detection signal match.

The first embodiment takes the form in which the useful life determining means also functions to warn that the sensor has come close to the end of its probable useful life. The present invention, however, can also take a form where the useful life determining means does not include such warning means. In such case, it is possible to arrange an exclusive warning means, separately from the useful life determining means, in order to let out a warning that the sensor has come close to the end of its probable useful life.

The first embodiment takes the form in which the destructive current supplying means uses the existing power source circuit that is necessary for the usual detecting operation by the sensor. The present invention, however, can also take a form where the destructive current supplying means does not use the existing power source circuit that is necessary for the usual detecting operation by the sensor, but includes an exclusive power source circuit for supplying the destructive current.

The first embodiment takes the form in which the disconnection detecting means is arranged for directly detecting as to whether a part of the circuit configuring the sensor has been disconnected. The present invention, however, can also take a form where the disconnection detecting means is not being arranged. In such case, possible disconnection can be detected indirectly by detecting the signal outputted from the useful life determining means for requesting the destructive current supplying means to supply destructive current, or by detecting the destructive current as supplied to the sensor from the destructive current supplying means.

The first embodiment takes the form in which the detecting means used for the usual detecting operation at the sensor also functions as the disconnection detecting means. The present invention, however, can also take a form where an exclusive disconnection detecting means is arranged separately from the detecting means as used for the usual detecting operation at the sensor.

What is claimed is:

1. An imperfect combustion detecting device comprising:
    a sensor which detects, when being energized, a CO level in combustion gas as generated at a burner in a combustion apparatus;
    a useful life determining means which compares a use limit value, which is a value corresponding to a predetermined probable useful life of the sensor and being stored in a memory section, with a deterioration status corresponding value, which is a value inputted depending on changes in deterioration status of the sensor, in order to determine as to whether the deterioration status corresponding value matches the use limit value; and
    a destructive current supplying means which supplies, under a condition in which it is determined by the useful life determining means that the deterioration status corresponding value matches the use limit value, destructive current to the sensor in order to destroy a circuit that configures the sensor.

2. The imperfect combustion detecting device according to claim 1, further comprising:
    a detecting circuit which detects as to whether the circuit configuring the sensor is broken and outputs the detected result.

3. The imperfect combustion detecting device according to claim 2, wherein
    the circuit configuring the sensor melts down and becomes disconnected due to being supplied with the destructive current, and
    the detecting circuit detects that a part of the circuit configuring the sensor is disconnected.

4. The imperfect combustion detecting device according to claim 2, further comprising:
    an announcing means which announces, under a condition in which it is determined by the useful life determining means that the deterioration status corresponding value matches a use limit warning value, that the sensor has come close to the end of its probable useful life,
    the use limit warning value being stored in the memory section as a value that is used in warning the coming of the end of probable useful life of the sensor.

5. The imperfect combustion detecting device according to claim 4, wherein
    the destructive current supplying means is configured as including a power source circuit which supplies the sensor with power for enabling the sensor to perform a CO level detecting function, and a voltage amplifying circuit which amplifies a voltage applied to the sensor by the power source circuit based on the determination made by the useful life determining means, and
    destructive current is supplied to the sensor from the power source circuit due to amplification operation performed by the voltage amplifying circuit.

6. The imperfect combustion detecting device according to claim 5, wherein
    the circuit configuring the sensor melts down and becomes disconnected due to being supplied with the destructive current, and
    the detecting circuit detects that a part of the circuit configuring the sensor is disconnected.

7. The imperfect combustion detecting device according to claim 4, wherein
    the circuit configuring the sensor melts down and becomes disconnected due to being supplied with the destructive current, and
    the detecting circuit detects that a part of the circuit configuring the sensor is disconnected.

8. The imperfect combustion detecting device according to claim 2, wherein
    the destructive current supplying means is configured as including a power source circuit which supplies the sensor with power for enabling the sensor to perform a CO level detecting function, and a voltage amplifying circuit which amplifies a voltage applied to the sensor by the power source circuit based on the determination made by the useful life determining means, and
    destructive current is supplied to the sensor from the power source circuit due to amplification operation performed by the voltage amplifying circuit.

9. The imperfect combustion detecting device according to claim 8, wherein
    the circuit configuring the sensor melts down and becomes disconnected due to being supplied with the destructive current, and
    the detecting circuit detects that a part of the circuit configuring the sensor is disconnected.

10. The imperfect combustion detecting device according to claim 1, further comprising:
    an announcing means which announces, under a condition in which it is determined by the useful life determining means that the deterioration status corresponding value matches a use limit warning value, that the sensor has come close to the end of its probable useful life,
    the use limit warning value being stored in the memory section as a value that is used in warning the coming of the end of the probable useful life of the sensor.

11. The imperfect combustion detecting device according to claim 10, wherein
    the destructive current supplying means is configured as including a power source circuit which supplies the sensor with power for enabling the sensor to perform a CO level detecting function, and a voltage amplifying circuit which amplifies a voltage applied to the sensor by the power source circuit based on the determination made by the useful life determining means, and
    destructive current is supplied to the sensor from the power source circuit due to amplification operation performed by the voltage amplifying circuit.

12. The imperfect combustion detecting device according to claim 1, wherein
    the destructive current supplying means is configured as including a power source circuit which supplies the sensor with power for enabling the sensor to perform a CO level detecting function, and a voltage amplifying circuit which amplifies a voltage applied to the sensor by the power source circuit based on the determination made by the useful life determining means, and
    destructive current is supplied to the sensor from the power source circuit due to amplification operation performed by the voltage amplifying circuit.

* * * * *